United States Patent
Chang et al.

(10) Patent No.: US 8,807,420 B2
(45) Date of Patent: Aug. 19, 2014

(54) FLOW CYTOMETER AND BIOCHIP DETECTING METHOD

(75) Inventors: Yao-Tsung Chang, New Taipei (TW); Pai-Yang Lin, New Taipei (TW)

(73) Assignee: Wistron Corporation, New Taipei (TW)

(*) Notice: Subject to any disclaimer, the term of this patent is extended or adjusted under 35 U.S.C. 154(b) by 217 days.

(21) Appl. No.: 13/430,714

(22) Filed: Mar. 27, 2012

(65) Prior Publication Data

US 2013/0126597 A1 May 23, 2013

(30) Foreign Application Priority Data

Nov. 22, 2011 (TW) .................................. 100142684

(51) Int. Cl.
*G06F 17/00* (2006.01)
*B01L 3/00* (2006.01)
*G01N 15/14* (2006.01)
*G01N 35/00* (2006.01)
*G01N 15/10* (2006.01)

(52) U.S. Cl.
CPC .............. *B01L 3/545* (2013.01); *G01N 15/147* (2013.01); *B01L 2300/023* (2013.01); *B01L 2300/02* (2013.01); *B01L 2300/0816* (2013.01); *G01N 2015/1006* (2013.01); *G01N 15/1484* (2013.01); *B01L 2300/024* (2013.01); *G01N 35/00623* (2013.01)
USPC .......................................... 235/375; 235/454

(58) Field of Classification Search
USPC ..................... 235/375, 454; 435/287.2, 288.7
See application file for complete search history.

(56) References Cited

U.S. PATENT DOCUMENTS

| | | | |
|---|---|---|---|
| 7,173,701 B2 * | 2/2007 | Wang et al. .................... | 356/417 |
| 7,888,125 B2 | 2/2011 | Gibbons et al. | |
| 2009/0032736 A1 * | 2/2009 | Tanaami .................... | 250/459.1 |
| 2009/0071829 A1 * | 3/2009 | O'Banion et al. ............ | 204/461 |

FOREIGN PATENT DOCUMENTS

| | | |
|---|---|---|
| CN | 101548184 | 9/2009 |
| JP | 2009008574 | 1/2009 |
| TW | 200824646 | 6/2008 |

OTHER PUBLICATIONS

"Office Action of Taiwan Counterpart Application", issued on Feb. 12, 2014, p. 1-p. 11, in which the listed references were cited.

* cited by examiner

*Primary Examiner* — Ahshik Kim
(74) *Attorney, Agent, or Firm* — Jianq Chyun IP Office

(57) ABSTRACT

A biochip detecting device for detecting a biochip which has identifying information is provided. The biochip detecting device has a controller, a reader, a storage medium and a detecting module. The reader reading the identifying information, the storage medium saving a detecting information, and the detecting module detecting the biochip are electrically connected to the controller. The controller is suitable for determining the record of the identifying information in the detecting information and modifying the setting of the detecting module automatically according to the identifying information. A biochip detecting method is further provided. A biochip detecting device is used to read identifying information of the biochip to determine whether the biochip could be detected. Besides, the setting of a detecting module is automatically adjusted by a controller. The time for adjusting the setting of the detecting module is saved and the possibility of setup mistake could be reduced.

20 Claims, 3 Drawing Sheets

FLOW CYTOMETER AND BIOCHIP DETECTING METHOD

CROSS-REFERENCE TO RELATED APPLICATION

This application claims the priority benefit of Taiwan application serial no. 100142684, filed Nov. 22, 2011. The entirety of the above-mentioned patent application is hereby incorporated by reference herein and made a part of this specification.

BACKGROUND OF THE INVENTION

1. Field of Invention

The present invention relates to a detecting device and a detection method. More particularly, the present invention relates to a biochip detecting device and a method for detecting a biochip.

2. Description of Related Art

Currently, the types of biochip detecting devices are vary and a flow cytometer is one of the tupes of the biochip detecting devices. The flow cytometer can classify cells suspended in the fluid and detect the physical properties of the cell.

When the flow cytometer is used to classify the cells, a certain amount of charges are optionally applied onto the cells and are redirected to different outlet while the cells pass through the electromagnetic field. Thus, the cells can be rapidly and accurately classified from the mixture.

When the flow cytometer is used to detect the physical properties, each of the cells suspended in the fluid passes through the light beams, the light beams scatters and the cells are excited to emit fluorescent light with the frequency lower than the excitation light since there are more than one light sources and more than one photo sensor in the flow cytometer. The scattering light beams and the fluorescent light are recorded by the photo sensor. According to the detecting results of the photo sensors, the physical properties and the chemical properties of the cells can be calculated.

Generally, after the fluid containing the cells to be detected is disposed on the biochip, the biochip is placed into the flow cytometer. Since the current flow cytometer cannot recognize whether the biochip has been used, the operator may repeatedly use the same biochip without notice which leads to incorrect detecting result and ineffective management of the biochip usage status.

Moreover, as for different types of biochips, it is necessary for the operator to manually adjust different parameters such as voltage of the driving circuit, the wavelength of the laser and the wavelength range of the light beam received by the photo sensor. Hence, when detecting huge amount of biochips, the operator needs to spend a lot of time for adjusting the parameters. If the parameters are mistakenly inputted, it leads to detection failure.

SUMMARY OF THE INVENTION

The invention provides a biochip detecting device capable of determining whether the biochip has been used and automatically adjusting the detecting parameters according to different biochips.

The invention provides a method for detecting a biochip, in which the biochip detecting device is used to determine whether the biochip can be detected and automatically adjusts the detecting parameters according to different biochips.

The invention provides a biochip detecting device for detecting a biochip. The biochip has identifying information. The biochip detecting device comprises a controller, a reader, a storage medium and a detecting module. The reader is electrically connected to the controller and reads the identifying information. The storage medium is electrically connected to the controller and stores detecting information. The detecting module is electrically connected to the controller and detects the biochip. The controller determines a record of the identifying information in the detecting information and automatically adjusts a setting of the detecting module according to the identifying information.

The invention also provides a biochip detecting device for detecting a biochip. The biochip has identifying information, the biochip detecting device communicates with a host machine, the host machine comprises a first transmission module, a control unit and a storage unit, the first transmission module and the storage unit are electrically connected to the control unit and the storage unit stores detecting information. The biochip detecting device comprises a controller, a reader, a second transmission module and a detecting module. The reader is electrically connected to the controller and reads the identifying information. The second transmission module is electrically connected to the controller and corresponds to the first transmission module. The detecting module is electrically connected to the controller and detects the biochip. The controller determines a record of the identifying information in the detecting information and automatically adjusts a setting of the detecting module according to the identifying information.

The invention further provides a method for detecting a biochip. In the method, a reader of a biochip detecting device reads identifying information of a biochip. According to the identifying information, whether the biochip can be detected is determined. According to the identifying information, a controller of the biochip detecting device automatically adjusts a setting of a detecting module of the biochip detecting device. The detecting module detects the biochip.

Accordingly, in the biochip detecting device and the method for detecting the biochip of the present invention, by determining the identifying information, whether the biochip can be detected is determined which prevents the biochip from being repeatedly used. Moreover, by using the controller automatically adjusting the setting of the detecting module, the time for adjusting the setting of the detecting module can be decreased and the possibility of error setting can be decreased as well.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE PREFERRED EMBODIMENTS

Figure 1:
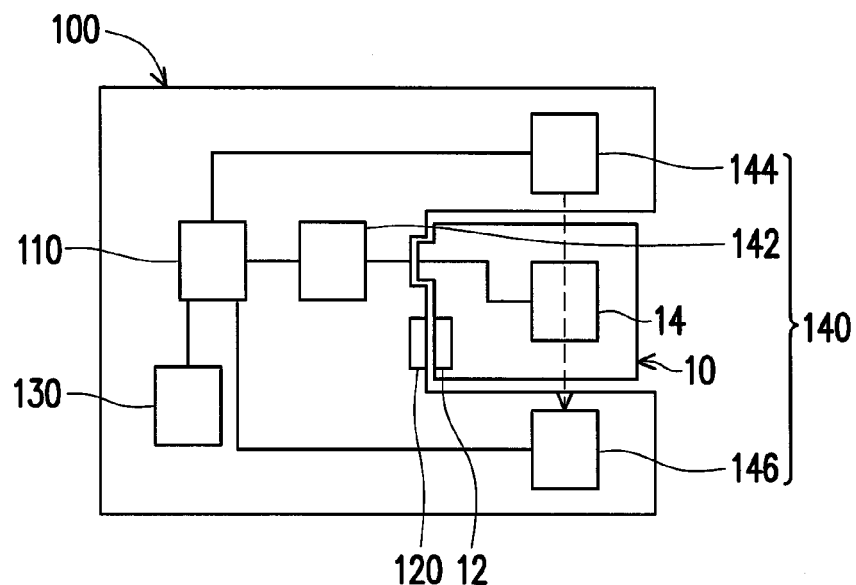
FIG. 1 is a schematic diagram showing a biochip detecting device and a biochip according to one embodiment of the invention.

The present invention provides a biochip detecting device. FIG. 1 is a schematic diagram showing a biochip detecting device and a biochip according to one embodiment of the invention. As shown in FIG. 1, the biochip 10 has identifying information 12. The biochip detecting device 100 of the present embodiment is a flow cytometer but the type of the biochip detecting device 100 is not limited thereto. The biochip detecting device 100 comprises a controller 110, a reader 120, a storage medium 130 and a detecting module 140. The reader 120 is electrically connected to the controller 110 and reads the identifying information 12. The detecting module 140 is electrically connected to the controller and detects the biochip 10. The storage medium 130 is electrically connected to the controller and stores detecting information.

Before detecting the biochip 10, the biochip detecting device 100 uses the reader 120 to read the identifying information 12 of the biochip 10 and to transmit the identifying information to the controller 110 to determine whether the biochip 10 can be applied onto the current biochip detecting device 100. Thus, it prevents the biochip from being misplaced in the biochip detecting device while the type of the biochip mismatches the biochip detecting device, the time for detecting the biochip can be saved and even the biochip detecting device can be protected from being damaged.

If the biochip 10 can be applied onto the current biochip detecting device 100, the controller 110 determines the record of the identifying information 12 in the detecting information in order to check whether the biochip 10 has been used before. The biochip 10 should be used just once so that the biochip 10 has been contaminated if it has been detected. The used biochip 10 should not be used in a second detection. The biochip detecting device 100 of the present embodiment can prevent from repeatedly detecting the same biochip 10.

The identifying information 12 comprises a chip serial number, a chip type or a sample number. If the biochips are given numbers and each of the biochips possesses it's own chip serial number, it is convenient for the controller 110 to determine whether the biochip 10 has been detected. Since the biochip detecting device 100 can perform different detections in accordance with different chip types, the detecting parameters, such as voltage of the driving circuit 142, a type of a light beam from the light source, 144 a wavelength of the light beam from the light source 144, and a detecting range of the photo sensor 146, are adjusted according to different chip types. Moreover, the sample number can be the identification number of the provider providing the cell to be detected. Thus, the operator can be aware of the information that the current detected biochip belongs to which provider. Off course, the type of the identifying information 12 is not limited to the above description.

If there is no record shows that the biochip has been detected, the controller 110 automatically adjusts the setting of the detecting module 140 according to the content of the identifying information 12. Hence, the time for manually adjusting the parameters can be saved and the possibility for wrongly inputting parameters can be decreased. The detecting module 140 uses the adjusted parameters to detect the biochip 10. After the detection is finished, the detecting result of the biochip 10 and the detection record are transmitted to the storage medium 130 so that the biochip 10 can be prevented from being detected again.

In the present embodiment, the detecting module 140 comprises a driving circuit 142, a light source 144 and a photo sensor 146. The driving circuit 142, the light source 144 and the photo sensor 146 are electrically connected to the controller 110. The biochip 10 comprises a fluid path 14 and the controller 110 controls the driving circuit 142 to send out a driving signal. The driving signal is transmitted to the biochip 10 through a transmission interface in order to drive the fluid on the fluid path 14. Moreover, the light beam emitted from the light source 144 passes through the fluid on the fluid path 14 and enters into the photo sensor 146.

Figure 2:
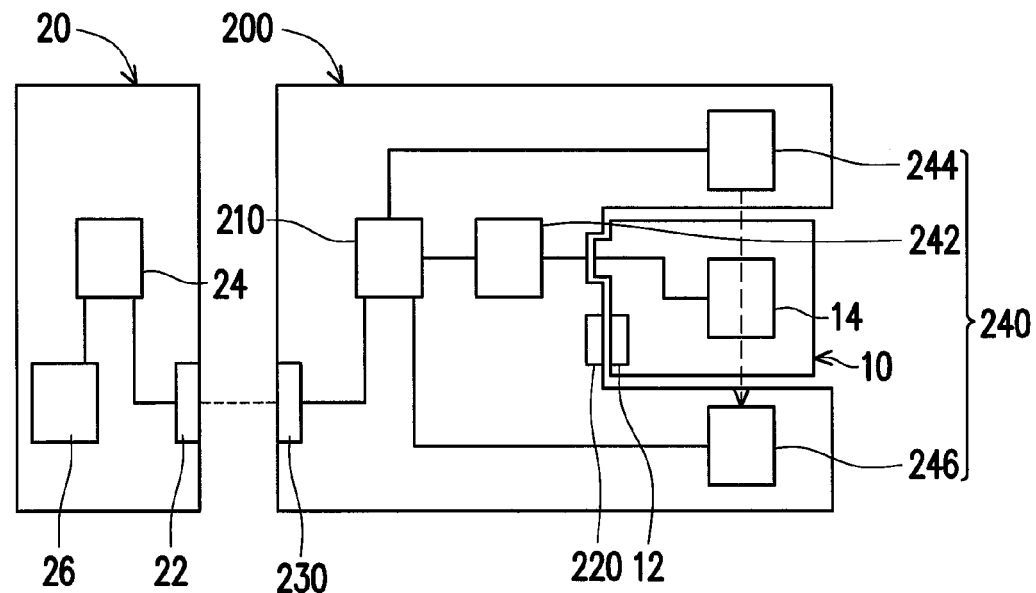
FIG. 2 is a schematic diagram showing a biochip detecting device and a biochip according to another embodiment of the invention.

FIG. 2 is a schematic diagram showing a biochip detecting device and a biochip according to another embodiment of the invention. As shown in FIG. 2, the biochip detecting device 200 of the present embodiment is used to detect a biochip 10. The biochip detecting device 200 of the present embodiment is a flow cytometer but the type of the biochip detecting device 200 is not limited thereto. The biochip 10 has identifying information 12 and the biochip detecting device 200 communicates with a host 20. The host 20 comprises a first transmission module 22, a control unit 24 and a storage unit 26. The first transmission module 22 and the storage unit 26 are electrically connected to the control unit 24 and the storage unit 26 stores a detecting information.

The biochip detecting device 200 comprises a controller 210, a reader 220, a second transmission module 230 and a detecting module 240. The reader 220 is electrically connected to the controller 210 and reads the identifying information 12. The second transmission module 230 is electrically connected to the controller 210 and corresponds to the first transmission module 22. The detecting module 240 is electrically connected to the controller 210 and detects the biochip 10. The controller 210 is used to determine a record of the identifying information in the detecting information and the controller 210 automatically adjusts the setting of the detecting module 240 according to the identifying information 12.

Before the biochip 10 is detected, the biochip detecting device 200 determines whether the biochip 10 can be applied onto the current biochip detecting device 200. The biochip detecting device 200 uses the reader 220 to read the identifying information 12 of the biochip 10 and transmits the identifying information 12 to the controller 210 in order to determine whether the biochip 10 can be applied onto the current biochip detecting device 200. Thus, it prevents the biochip from being misplaced in the biochip detecting device while the type of the biochip mismatches with the biochip detecting device.

If the biochip 10 can be applied onto the current biochip detecting device 200, the identifying information 12 is transmitted to the first transmission module 22 through the second transmission module 230. In the present embodiment, the second transmission module 230 and the first transmission module 22 can transmit signals in a way of cable transmission or wireless transmission, and the host 20 can be a computer or a server. The controller 210 compares the identifying information 12 with the detecting information stored in the storage unit 26 of the host 20 to determine whether the biochip 10 has been detected. If there is no detecting information of the biochip 10 in the storage device 26, the controller 210 automatically adjusts the setting of the detecting module 240 according to the identifying information 12 and the detecting module 240 uses the adjusted parameters to detect the biochip 10.

In the present embodiment, the detecting module 240 comprises a driving circuit 242, a light source 244 and a photo sensor 246. The driving circuit 242, the fight source 244 and the photo sensor 246 are electrically connected to the controller 210. The biochip 10 comprises a fluid path 14 and the controller 210 controls the driving circuit 242 to send out a driving signal. The driving signal is transmitted to the biochip 10 through a transmission interface in order to drive the fluid on the fluid path 14. Moreover, the light beam emitted from the light source 244 passes through the fluid on the fluid path 14 and enters into the photo sensor 246.

After the detection, the detecting result of the biochip 10 can be uploaded to the storage unit 26 of the host 20. Since different biochip detecting devices 200 can be connected to the same host 20, the identifying information 12 of the detected biochips 10 respectively detected by different biochip detecting devices 200 are transmitted to the host 20. The control unit 24 compares the identifying information 12 with the detecting information stored in the storage unit 26 of the host 20 to know whether the biochip 10 has been detected. Thus, it can prevent the biochip from being repeatedly detected by different biochip detecting devices 200. In addition, since the storage unit 26 of the host 20 stores a relatively large amount of detecting results, it is easy to perform the statistic of the detecting result.

The difference between the embodiment shown in FIG. 2 and the embodiment shown in FIG. 1 includes that, in the embodiment shown in FIG. 2, the detecting information is stored in the host 20 and different biochip detecting devices 200 can connect to the same host 20. The embodiment shown in FIG. 2 uses the control unit 24 of the host 20 to determine whether the biochip 10 has been used before. In the embodiment shown in FIG. 1, the detecting information is stored in the storage medium 130 and the controller 110 is used to determine whether the biochip 10 has been used before.

In the present embodiment, the identifying information 12 comprises a chip type, a chip serial number and a sample number. The control unit 24 can directly read the chip serial number to determine whether the biochip 10 has been detected. The control module 210 adjusts the detecting parameters in accordance with different chip types. If the sample number is the identification number of the provider providing the cell to be detected, the operator not only knows the information that the current detected biochip 10 belongs to which provider but also correlates the detecting result with the provider. If the sample to be detected is provided by a patient from a hospital, the doctor can be directly aware of the detecting result from the electronic anamnesis of the patient when the detecting result is ready. Thus, the processing rate is greatly improved.

Figure 3:
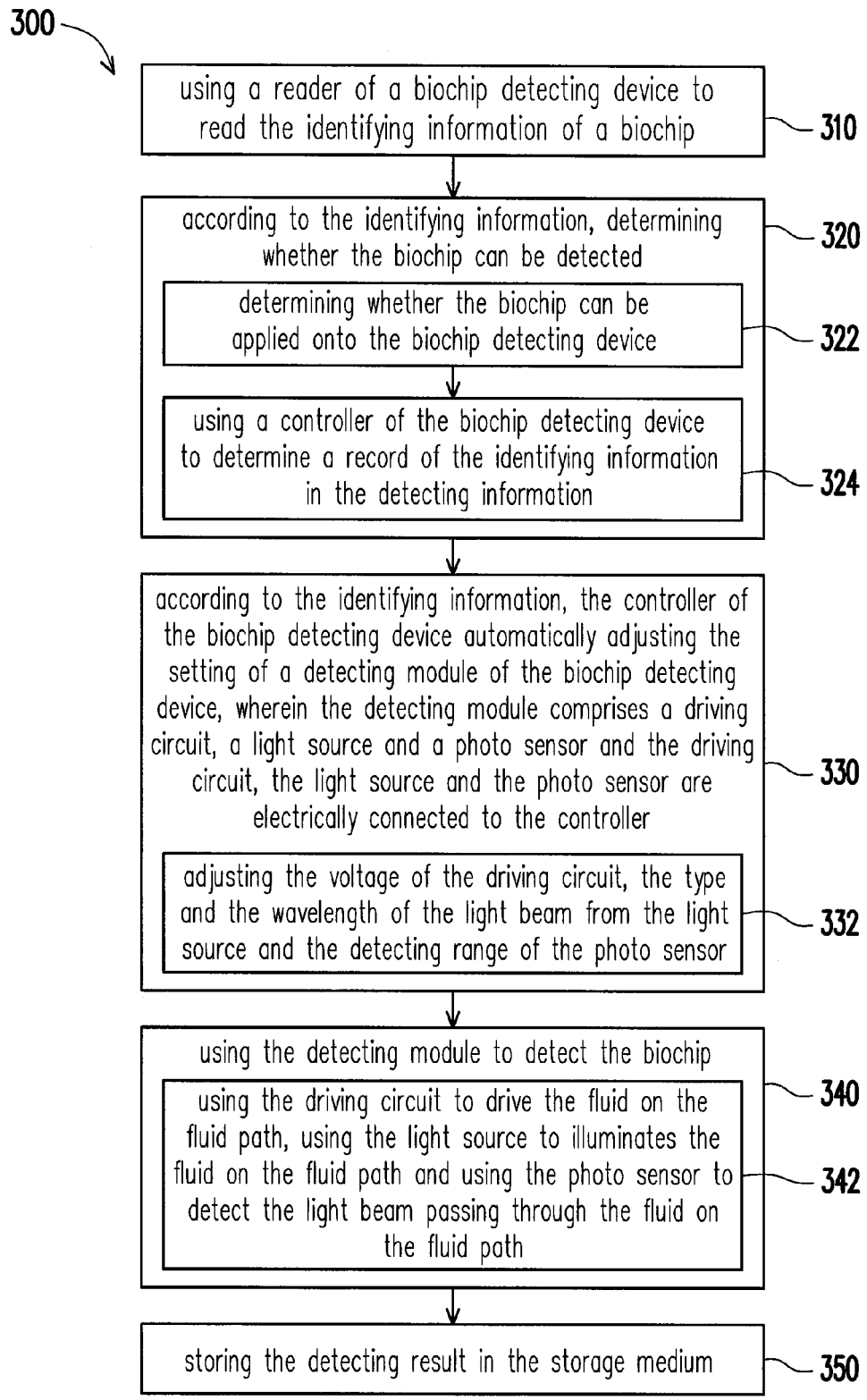
FIG. 3 is a flow chart illustrating a method for detecting a biochip according to one embodiment of the invention.

FIG. 3 is a flow chart illustrating a method for detecting a biochip according to one embodiment of the invention. As shown in FIG. 3, the method 300 for detecting a biochip of the present embodiment is illustrated as followings. Use a reader of a biochip detecting device to read the identifying information of a biochip (step 310). The identifying information comprises a chip type, a chip serial number or a sample number.

Then, according to the identifying information, it is determined whether the biochip can be detected (step 320). The biochip detecting device comprises a controller and a storage medium which is electrically connected to the controller and stores detecting information. The step of determining whether the biochip can be detected includes determining whether the biochip can be applied onto the biochip detecting device (step 322) and using the controller to determine a record of the identifying information in the detecting information (step 324).

Determining whether the biochip can be applied onto the biochip detecting device is to prevent the biochip from being misplaced in the biochip detecting device while the type of the biochip mismatches the biochip detecting device. Hence, the time for detecting the biochip can be saved and even the biochip detecting device can be protected from being damaged. Moreover, if the detecting information reveals that the biochip has been detected, the biochip detecting device not only stops detecting but also warns the operator. If the biochip has not been detected, the detection of the biochip continues.

In addition, according to the identifying information, the controller of the biochip detecting device automatically adjusts the setting of a detecting module of the biochip detecting device (step 330). The detecting module comprises a driving circuit, a light source and a photo sensor. The driving circuit, the light source and the photo sensor are electrically connected to the controller. The step of adjusting the setting of the detecting module includes adjusting the voltage of the driving circuit, the type and the wavelength of the light beam from the light source and the detecting range of the photo sensor (step 332).

Then, use the detecting module to detect the biochip (step 340). The biochip comprises a fluid path. The step of detecting the biochip includes using the driving circuit to drive the fluid on the fluid path, using the light source to illuminates the fluid on the fluid path and using the photo sensor to detect the light beam passing through the fluid on the fluid path (step 342).

Finally, store the detecting result in the storage medium (step 350). In the present step, the information about the biochip having been used is also stored in the storage medium. Thus, in the future, if the biochip is detected again, the information about the biochip having been used is obtained while the controller determines the record of the identifying information in the detecting information. Therefore, it effectively prevents the biochip from being repeatedly used.

Figure 4:
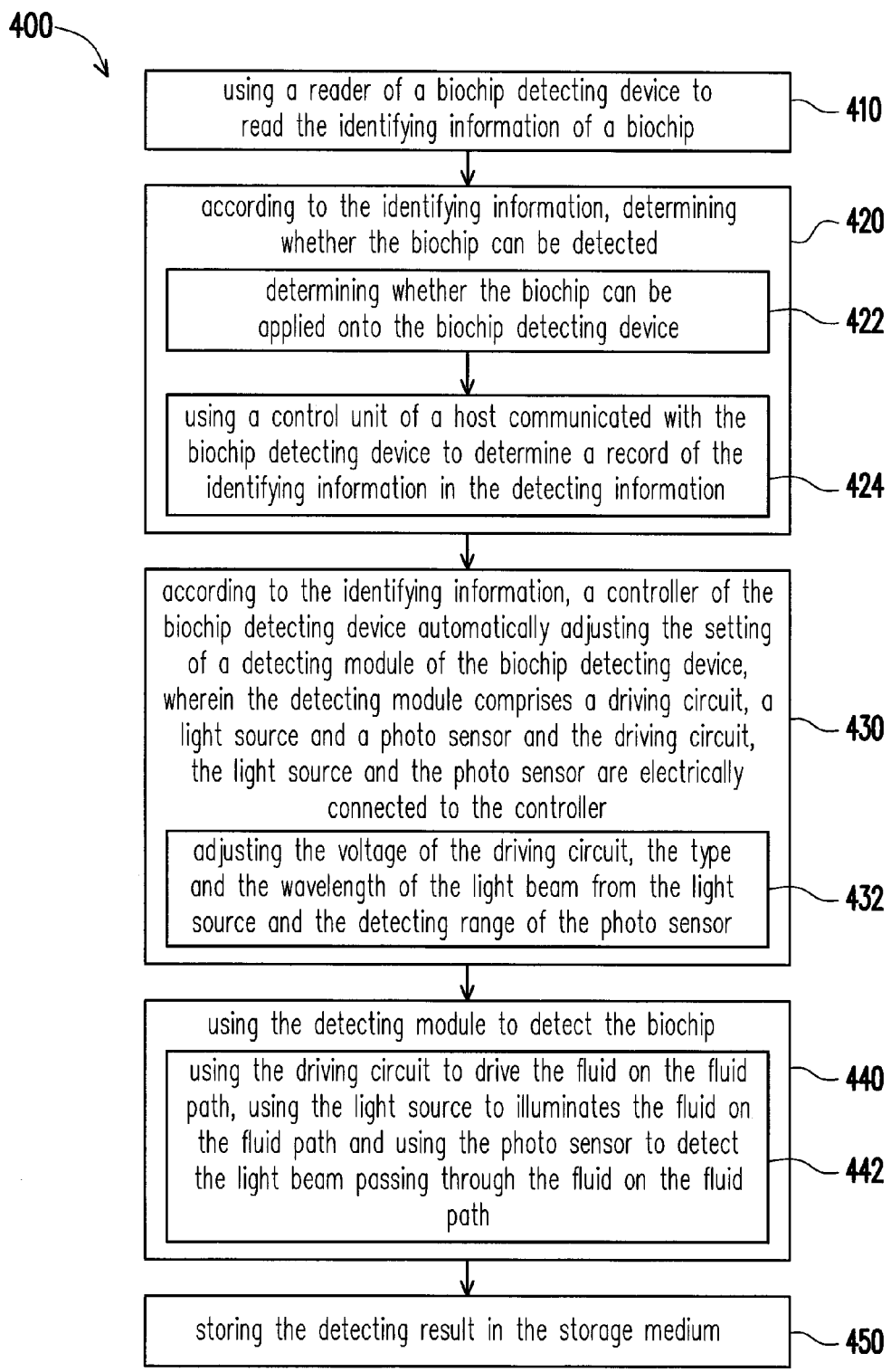
FIG. 4 is a flow chart illustrating a method for detecting a biochip according to another embodiment of the invention.

FIG. 4 is a flow chart illustrating a method for detecting a biochip according to another embodiment of the invention. The method 400 for detecting a biochip of the present embodiment is illustrated as followings. Use a reader of a biochip detecting device to read the identifying information of a biochip (step 410).

Then, according to the identifying information, it is determined whether the biochip can be detected (step 420). The biochip detecting device of the present embodiment communicates with a host and the host comprises a first transmission module, a control unit and a storage unit. The first transmission module, the storage unit are electrically connected to the control unit. The storage unit stores detecting information and the biochip detecting device comprises a second transmission module and a controller electrically connected to the second transmission module. The step of determining whether the biochip can be detected includes determining whether the biochip can be applied onto the biochip detecting device (step 422) and using the control unit to determine a record of the identifying information in the detecting information (step 424).

If it is found out from the detecting information that the biochip has been detected, the biochip detecting device not only stops detecting but also warns the operator. If the biochip has not been detected, the detection of the biochip continues.

Additionally, according to the identifying information, the controller of the biochip detecting device automatically adjusts the setting of a detecting module of the biochip detecting device (step 430). The detecting module comprises a driving circuit, a light source and a photo sensor. The driving circuit, the light source and the photo sensor are electrically connected to the controller. The step of adjusting the setting of the detecting module includes adjusting the voltage of the driving circuit, the type and the wavelength of the light beam from the light source and the detecting range of the photo sensor (step 432).

Then, use the detecting module to detect the biochip (step 440). In the present embodiment, the biochip comprises a fluid path. The step of detecting the biochip includes using the driving circuit to drive the fluid on the fluid path, using the light source to illuminates the fluid on the fluid path and using the photo sensor to detect the light beam passing through the fluid on the fluid path (step 442).

Finally, store the detecting result in the storage medium (step 450). In the present step, the information about the biochip having been used is also stored in the storage medium.

The difference between the embodiment shown in FIG. 4 and the embodiment shown in FIG. 3 is that, in FIG. 4, different biochip detecting devices can be connected to the same host, the detecting information is stored in the storage unit of the host and the control unit of the host is used to determine whether the biochip has been used. In the embodiment shown in FIG. 3, the detecting information is stored in the storage medium of the biochip detecting device and the controller of the biochip detecting device is used to determine whether the biochip has been used.

Accordingly, the biochip detecting device and the method for detecting the biochip of the present invention determines whether the biochip can be detected by determining the identifying information so that it prevents the biochip from being repeatedly used. Also, the biochip detecting device and the method for detecting the biochip of the present invention can effectively manage the usage status of the biochips. Moreover, the biochip detecting device and the method for detecting the biochip of the present invention automatically adjust the setting of the detecting module through the controller so as to decrease the time for adjusting the setting of the detecting module and eliminating the possibility of setup mistake.

It will be apparent to those skilled in the art that various modifications and variations can be made to the structure of the present invention without departing from the scope or spirit of the invention. In view of the foregoing descriptions, it is intended that the present invention covers modifications and variations of this invention if they fall within the scope of the following claims and their equivalents.

What is claimed is:

1. A flow cytometer for detecting a biochip, wherein the biochip has identifying information, the flow cytometer comprising:
    a controller;
    a reader, electrically connected to the controller and reading the identifying information;
    a storage medium, electrically connected to the controller and storing detecting information; and
    a detecting module, electrically connected to the controller and detecting the biochip, wherein:
    the controller determines a record of the identifying information in the detecting information and automatically adjusts a setting of the detecting module according to the identifying information.

2. The flow cytometer of claim 1, wherein the detecting module comprises a driving circuit, a light source and a photo sensor and the driving circuit, the light source and the photo sensor are electrically connected to the controller.

3. The flow cytometer of claim 2, wherein the biochip comprises a fluid path, the driving circuit drives fluid on the fluid path and a light beam from the light source passes through the fluid on the fluid path and enters into the photo sensor.

4. The flow cytometer of claim 1, wherein the identifying information comprises a chip type, a chip serial number or a sample number.

5. A flow cytometer for detecting a biochip, wherein the biochip has identifying information, the flow cytometer communicates with a host machine, the host machine comprises a first transmission module, a control unit and a storage unit, the first transmission module and the storage unit are electrically connected to the control unit and the storage unit stores detecting information, the flow cytometer comprising:
    a controller;
    a reader, electrically connected to the controller and reading the identifying information;
    a second transmission module, electrically connected to the controller and corresponding to the first transmission module; and
    a detecting module, electrically connected to the controller and detecting the biochip, wherein:
    the controller determines a record of the identifying information in the detecting information and automatically adjusts a setting of the detecting module according to the identifying information.

6. The flow cytometer of claim 5, wherein the detecting module comprises a driving circuit, a light source and a photo sensor and the driving circuit, the light source and the photo sensor are electrically connected to the controller.

7. The flow cytometer of claim 6, wherein the biochip comprises a fluid path, the driving circuit drives fluid on the fluid path and a light beam from the light source passes through the fluid on the fluid path and enters into the photo sensor.

8. The flow cytometer of claim 5, wherein the identifying information comprises a chip type, a chip serial number or a sample number.

9. A method for detecting a biochip, comprising:
    using a reader of a flow cytometer to read identifying information of a biochip;
    according to the identifying information, determining whether the biochip can be detected;
    according to the identifying information, a controller of the flow cytometer automatically adjusting a setting of a detecting module of the flow cytometer; and
    using the detecting module to detect the biochip.

10. The method of claim 9, wherein the step of determining whether the biochip can be detected comprises determining whether the biochip can be applied onto the flow cytometer.

11. The method of claim 9, wherein the flow cytometer comprises a storage medium electrically connected to the controller and storing detecting information.

12. The method of claim 11, wherein the step of determining whether the biochip can be detected comprises determining a record of the identifying information in the detecting information by using the controller.

13. The method of claim 11, further comprising storing a detecting result of the biochip in the storage medium.

14. The method of claim 9, wherein the flow cytometer communicates with a host machine, the host machine comprises a first transmission module, a control unit and a storage unit, the first transmission module and the storage unit are electrically connected to the control unit, the storage unit stores detecting information and the flow cytometer comprises a second transmission module electrically connected to the controller.

15. The method of claim 14, wherein the step of determining whether the biochip can be detected comprises determining a record of the identifying information in the detecting information by using the control unit.

16. The method of claim 14, further comprising storing a detecting result of the biochip in the storage unit.

17. The method of claim 9, wherein the detecting module comprises a driving circuit, a light source and a photo sensor, the driving circuit, the light source and the photo sensor are electrically connected to the controller and the biochip comprises a fluid path.

18. The method of claim 17, wherein the step of automatically adjusting the setting of the detecting module comprises adjusting a voltage of the driving circuit, a type of a light beam from the light source, a wavelength of the light beam from the light source, and a detecting range of the photo sensor.

19. The method of claim 17, wherein the step of detecting the biochip comprises using the driving circuit to drive fluid on the fluid path, the light source illuminating a light beam on the fluid on the fluid path and the photo sensor detecting the light beam passing through the fluid on the fluid path.

20. The method of claim 9, wherein the identifying information comprises a chip type, a chip serial number or a sample number.

* * * * *